United States Patent [19]

Birum

[11] 3,980,618

[45] Sept. 14, 1976

[54] CYCLIC ORGANOPHOSPHORUS AMIDES

[75] Inventor: Gail H. Birum, Kirkwood, Mo.

[73] Assignee: Monsanto Company, St. Louis, Mo.

[22] Filed: June 2, 1975

[21] Appl. No.: 582,963

Related U.S. Application Data

[63] Continuation-in-part of Ser. No. 385,933, Aug. 6, 1973, Pat. No. 3,904,654.

[52] U.S. Cl. .................................. 260/551 P; 71/86; 71/87; 106/15 FP; 252/8.1; 260/347.2; 260/347.8; 260/465 E; 260/502.5; 260/552 R; 260/553 A; 260/936
[51] Int. Cl.[2] .......................... C07F 9/24; C07F 9/44
[58] Field of Search ................................. 260/551 P

[56] References Cited
UNITED STATES PATENTS

| | | | |
|---|---|---|---|
| 3,522,303 | 7/1970 | Ulrich | 260/551 P |
| 3,673,248 | 6/1972 | Petersen | 260/543 PN |
| 3,846,374 | 11/1974 | Farley et al. | 260/551 P |

OTHER PUBLICATIONS
Merten et al., CA 71: 30549u (1969).

*Primary Examiner*—Daniel E. Wyman
*Assistant Examiner*—Thomas A. Waltz

[57] ABSTRACT

The present invention relates to new compounds containing urea and organophosphorus amide moieties in cyclic structures as shown in the following equation:

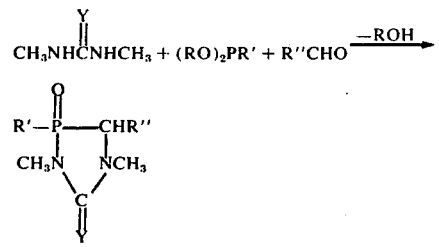

where
R is aryl or chloroalkyl of 2 to 10 carbon atoms,
R' is aryl of 6 to 10 carbon atoms,
R'' is hydrogen, alkyl, alkenyl, furanyl or aryl of 1 to 15 carbon atoms and substituted aryl forms where the substituent is fluorine, chlorine, bromine, cyano, hydroxyl, alkyloxy, alkylthio or mixtures of such substituents, and
Y is O or S.

The cyclic organophosphorus amides have biological activity and are also useful as fire retardants and as lead scavengers in gasoline.

6 Claims, No Drawings

CYCLIC ORGANOPHOSPHORUS AMIDES

The present patent application is a continuation-in-part of Ser. No. 385,933, filed Aug. 6, 1973 now U.S. Pat. No. 3,904,654.

The present invention relates to new compounds containing urea and organophosphorus amide moieties in cyclic structures.

The general method for the production of the novel cyclic organophosphorus amides is in accordance with the following equation:

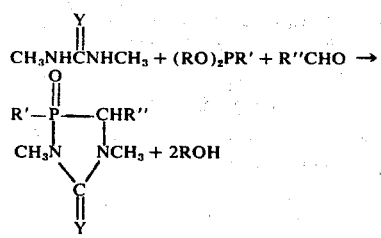

where
R is aryl or chloroalkyl of 2 to 10 carbon atoms,
R' is aryl of 6 to 10 carbon atoms,
R'' is hydrogen, alkyl, alkenyl, furanyl or aryl of 1 to 15 carbon atoms and substituted aryl forms where the substituent is fluorine, chlorine, bromine, cyano, hydroxyl, alkoxy, alkylthio or mixtures of such substituents, and
Y is O or S.

A specific compound is 3-(2,4-dichlorophenyl)-1,4-dimethyl-2-phenyl-1,4,2-diazaphospholidin-5-one-2-oxide which is prepared from 1,3-dimethylurea, diphenyl phenylphosphonite, and 2,4-dichlorobenzaldehyde according to the following equation:

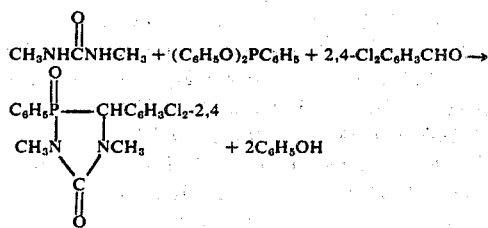

Free acids of the corresponding cyclic organophosphorus amides discussed above can be produced by ring-opening hydrolysis reactions. Thus, when a cyclic phosphorus amide is hydrolyzed, an open-chain phosphinic acid is produced according to the following equation:

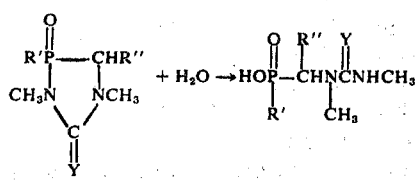

where
R' is aryl of 6 to 10 carbon atoms,
R'' is alkyl, alkenyl, furanyl or aryl of 1 to 15 carbon atoms and substituted aryl forms where the substituent is fluorine, chlorine, bromine, cyano, hyroxyl, alkyloxy, alkylthio or mixtures of such substituents, and
Y is O or S.

The use of basic materials in the hydrolysis mixture, for example dilute aqueous sodium hydroxide, may aid in the hydrolysis reaction. In such cases the initial hydrolysis products are salts, and these can be converted to the free phosphinic acids by acidification of the hydrolysis reaction mixture.

A specific example of the phosphinic acids is [α-(1,3-dimethylureido)-2,4-dichlorobenzyl]phenylphosphinic acid,

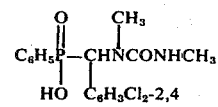

Formation of the cyclic products of this invention is usually initiated when a mixture of the three reactants, preferably in an inert solvent such as toluene or chlorobenzene, is warmed to about 70°C. The reaction is usually complete after an hour at 80°–120°C., but warming at higher or lower temperatures is sometimes advantageous. Gradual addition of the aldehyde reactant to a stirred mixture of the phosphoroous ester and 1,3-dimethylurea reactants in a solvent at reaction temperature, usually from about 70° to 120°C., may facilitate control of heat of reaction.

The cyclic products may be isolated from the reaction mixtures and purified by standard techniques before being subjected to hydrolysis to the corresponding acids. However, it is frequently more convenient to treat the crude, unisolated product in the reaction mixture with the required amount of water and then stir and warm the mixture until the desired hydrolysis is complete. The low solubility of the free acids in the reaction mixtures usually makes the acids easier to isolate than the parent cyclic structures.

Specific examples showing the preparation and isolation of representative compounds of the present invention are set forth herewith, but are not limitative of the scope of the invention.

EXAMPLE 1

3-(2,4-Dichlorophenyl)-1,4-dimethyl-2-phenyl-1,4,2-diazaphospholidin-5-one-2-oxide

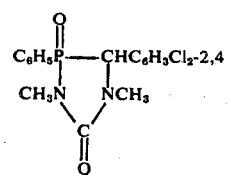

A solution of 0.3 mole each of diphenyl phenylphosphonite, 2,4-dichlorobenzaldehyde, and 1,3-dimethylurea in 150g of toluene is stirred under $N_2$ and warmed at 100°–110° for 2 hr. The resulting solution has $^{31}P$ nmr peaks at −30.6 and −26.3 ppm ~2:1 areas). The solvent and most of the by-product phenol are removed by stripping to 120°/1mm, and the residue is diluted with ether which causes separation of white solid (I), mp 204°–206° (from $CH_3CN$). Additional solid (II), mp 205°–207.5°, is isolated from the filtrate.

There is marked depression of the mixed melting point of I and II and appreciable differences in their nmr spectra. For I: $^{31}$P nmr −28.9 ppm (in CDCl$_3$), −38.6 ppm (in CF$_3$CO$_2$H); $^1$H nmr (CDCl$_3$) δ7.3 (m, 8, aryl), 5.2 (d, 1, J = 22Hz, PCH), 3.1 (s, 3, CH$_3$NCH), 2.9 (d, 3, J = 8Hz, PNCH$_3$); ms 370(6) (molecular ion), 368(10) (molecular ion), 335(10), 333(25), 311(6), 278(23), 276(100), 186(38), 124(43), 77(29). For II: $^{31}$P nmr −25.0 ppm (in CDCl$_3$), −32.9 ppm (in CF$_3$CO$_2$H); $^1$H nmr (CDCl$_3$) δ7.6 (m, 8, aryl), 5.2 (d, 1, J = 9Hz, PCH), 2.9 (s, 3, CHNCH$_3$), 2.85 (d, 3, J = 8Hz, PNCH$_3$) (decoupling from $^{31}$P converted the doublets at 5.2 and 2.85 ppm to singlets); ms 370(1), 368(1), 335 (12), 333(66), 311(2), 278(13), 276(100), 186(29), 124(32), 77(13).

Anal. (II) Calcd for C$_{16}$H$_{15}$N$_2$Cl$_2$O$_2$P: C, 52.05; H, 4.10; Cl, 19.21; N, 7.59; P, 8.39. Found: C, 52.33; H, 4.14; Cl, 18.82; N, 7.50; P, 8.31.

EXAMPLE 2

1,4-Dimethyl-2-(4-methylphenoxy)-3-phenyl-1,4,2-diazaphospholidin-5-one-2oxide

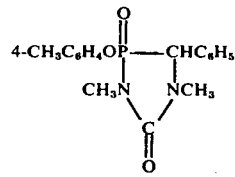

Benzaldehyde, 0.5 mole, is added dropwise to a solution of 0.5 mole of 1,3-dimethylurea and 0.5 mole of tris(p-tolyl)phosphite in 100 g of benzene as the solution was warmed from 60°–90°. Warming is continued at 90° for 3 hr, giving a reaction mixture having $^{31}$P nmr peaks at −24.2 and −21.9 ppm (∼6:1 areas). The solvent and most of the by-product p-cresol are removed by stripping to 120°/0.5mm, and the remaining yellow, viscous oil is dissolved in acetone. A solid that separates is recrystallized from acetone to give a white solid: mp 126.5°–128°; $^{31}$P nmr −24.2 ppm; $^1$H nmr δ6.9–7.5 (m, 9, aryl), 4,6 (d, 1, J = 19Hz, PCH), 2.9 (d, 3, J = 8Hz, PNCH$_3$), 2.7 (s, 3, NCH$_3$), 2.3 (s, 3, CH$_3$); ms 330(50) (molecular ion), 273(1), 224(4), 239(6), 223(27), 182(4), 166(100), 118(49), 107(5), 91(17), 77(14), 60(42).

Anal. Calcd for C$_{17}$H$_{19}$N$_2$O$_3$P: C, 61.18; H, 5.80; N, 8.48; P, 9.38. Found: C, 61,81; H, 5.67; N, 8.33; P, 9.33.

EXAMPLE 3

1,4-Dimethyl-2,3-diphenyl-1,4,2-diazaphospholidin-5-one-2-oxide

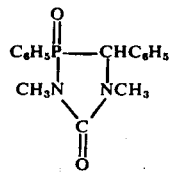

A solution of 0.3 mole each of bis(chloropropyl)-phenylphosphonite, 1,3-dimethylurea, and benzaldehyde in 100g of toluene is warmed at 105°–110° for 1.5 hr, giving a light yellow reaction mixture in which about half of the phosphorus detectable by nmr had a chemical shift at −25.9 ppm. Stripping to 107°/0.5mm followed by dilution with ether and filtration gives 14.8g of white solid: mp 132°–138° (141.5°–143.5° from tetrahydrofuran-ether); $^{31}$P nmr −25.6 ppm; $^1$H nmr δ7.3 and 7.6 (m, 10, aryl), 4.6 (d, 1, J = 6Hz, CH), 2.9 (d, 3, J = 8Hz, CH$_3$NP), 2.8 (s, 3, CH$_3$NCH) (phosphorus decoupling converted both doublets to singlets); mass spectrum (70 eV) m/e(rel intensity) 300(27) (molecular ion), 243(67), 228(35), 166(15), 124(30), 118(100), 77(38), 60(15).

Anal. Calcd for C$_{16}$H$_{17}$N$_2$O$_2$P: C, 63.98; H, 5.70; N, 9.33; P, 10.31. Found: C, 63.70; H, 5.75; N, 9.06; P, 10.40.

EXAMPLE 4

1,4-Dimethyl-3-(3,4-dichlorophenyl)-2-phenoxy-1,4,2-diazaphospholidin-5-thione-2-oxide.

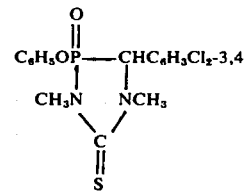

A solution of 0.3 mole each of 1,3-dimethylthiourea, 3,4-dichlorobenzaldehyde, and triphenyl phosphite in 75g of toluene is warmed at 120°–125° for 1.25 hr, giving a yellow solution having $^{31}$P nmr signals at −27.5 and −24.7 ppm (∼5:1 areas). The reaction mixture is stripped to 110°/0.5mm to remove the solvent and most of the by-product phenol. Two-thirds of the resulting yellow oil is diluted with ether, kept at 5° for 12 hr and filtered, giving 35.2g of white solid: mp 125°–126° (from butyl acetate); $^{31}$P nmr −26.6 ppm; $^1$H nmr δ7.2 (m, 8, aryl), 4.7 (d, 1, J = 18Hz, CH), 3.1 (d, 3, J = 7Hz, CH$_3$NP), 3.1 d, 3, J = 1Hz, CH$_3$NCH); ir(KBr) 2.9(m), 6.24(w), 6.68(s), 7.20(m), 7.53(s), 7.87(s), 8.37(s), 10.68μ(vs); ms 400 and 402(100) (molecular ions), 327 and 329(8), 307 and 309(3), 298 and 300(72), 186 and 188(69), 159 and 161(50).

Anal. Calcd for C$_{16}$H$_{15}$Cl$_2$N$_2$O$_2$PS: C, 47.89; H, 3.77; Cl, 17.67; N, 6.98; P, 7.72; S, 7.99. Found: C, 47.90; H, 3.87; Cl, 17.93; N, 6.94; P, 7.71; S, 7.93.

The remaining one-third of the yellow oil is dissolved in 100ml of acetonitrile and 15g of H$_2$O, and this solution is refluxed for 1 hr. After standing 15 hr at room temperature, the reaction mixture is filtered, and the solid is extracted with hot acetonitrile, giving 17.8g. Recrystallization from acetic acid-water gives 13.5g of α-(1,3-dimethylthioureido)-3,4-dichlorobenzylphosphonic acid: white solid; mp 178°–179° dec; $^{31}$P nmr (CD$_3$SOCD$_3$) −15.1 ppm (d, J = 24Hz); $^1$H δ8.5 (s, 3, HO and NH), 7.7 (m, 3, aryl), 7.2(d, 1, J = 24Hz, CH), 3.1 and 3.0 (s, 6, CH$_3$); ir(KBr) 3.02μ(m), 3.51(m), 6.45(s), 6.78(m), 7.32(s), 7.90(s); acidity, 2.00 equiv/mole, pK$_1$ = 3.20, pK$_2$ = 8.65.

Anal. Calcd for C$_{10}$H$_{13}$Cl$_2$N$_2$O$_3$PS: C, 34.99; H, 3.82; Cl, 20.66; N, 8.16; P, 9.02; S, 9.34. Found: C, 34.89; H, 4.25; Cl, 20.84; N, 8.15; P, 8.81; S, 9.25.

EXAMPLE 5

3-(4-Cyanophenyl)-1,4-dimethyl-2-phenyl-1,4,2-diazaphospholidin-5-one-2-oxide

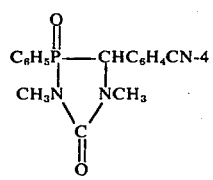

A mixture of 0.12 mole each of 4-cyanobenzaldehyde, 1,3-dimethylurea, and diphenyl phenylphosphonite in 150ml of toluene is warmed at reflux (112°) for 3.5 hr and then stripped to 120°/10mm, leaving a viscous, light yellow oil having $^{31}$P nmr peaks at −31.2 and −25.7 ppm (~2:1 areas). Dilution of the oil with ether results in separation of a solid from which two isomers are isolated by fractional crystallization. Isomer I: mp 176°–179°; $^{31}$P nmr (CDCl$_3$) −30.6 ppm; $^1$H nmr δ7.3 (m, 9, aryl), 5.1 (d, 1, J = 22Hz, PCH), 3.0 (s, 3, NCH$_3$), 2.95 (d, 3, J = 8Hz, PNCH$_3$), Isomer II: mp 180°–182.5°; $^{31}$P nmr −26.7 ppm; $^1$H nmr δ7.8 (m, 9, aryl), 4.7 (d, 1, J = 7Hz, PCH), 2.9 (s, 3, NCH$_3$), 2.9 (d, 3, J = 8Hz, PNCH$_3$). There is a sharp depression of the mixed melting point of I and II.

EXAMPLE 6

2-(2-Chloroethoxy)-1,4-dimethyl-3-phenyl-1,4,2-diazaphospholidin-5-one-2-oxide

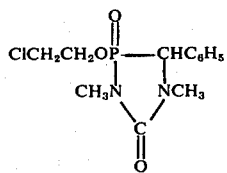

A mixture of 88.0g (1.0 mole) of 1,3-dimethylurea, 269.5g (1.0 mole) of tris(2-chloroethyl) phosphite, and 106.1g (1.0 mole) of benzaldehyde is stirred under nitrogen and warmed at 103°–106° for 3.5 hr, giving a light yellow solution: $^{31}$P nmr —139.0, −28.3, −22.8 (area ratio ~1:8:2). The by product ethylenechlorohydrin is stripped off to 105°/0.1mm, and 150ml of benzene is added. Solid separates as the reaction mixture cools. Recrystallization from acetonitrile gives 50.1g, mp 134°–135.5°. A second recrystallization from acetonitrile gives a white solid: mp 136°–137°; $^{31}$P nmr −28.5 ppm; $^1$H nmr δ7.3 (m, 5, aryl), 4.6 (d, 1, J = 19Hz, CH), 4.3 (m, 2, OCH$_2$), 3.7 (m, 2, CH$_2$Cl), 2.9 (d, 3, J = 8Hz, PNCH$_3$), 2.8 (s, 3, CH$_3$NCH); ir(KBr) 3.42(m), 5.78(s), 6.90(m), 7.22(m), 7.95(vs); mass spectrum (70 eV) m/e(rel intensity) 302(26) (molecular ion), 273(2), 245(9), 239(40), 216(6), 182(8), 166(5), 118(100), 91(14).

Anal. Calcd for C$_{12}$H$_{16}$ClN$_2$O$_3$P: C, 47.61; H, 5.33; Cl, 11.71; N, 9.25; P, 10.23. Found: C, 47.69; H, 5.25; Cl, 11.69; N, 9.34; P, 10.38.

The filtrates are combined and treated with 30g of water at reflux for 0.5 hr. Filtration of the warm reaction mixture and then extraction of the solid with warm acetonitrile gives 50.9g of α-(1,3-dimethylureido) benzylphosphonic acid: mp 178°–180° dec; $^{31}$P nmr (CD$_3$SOCD$_3$) −18.2 ppm; $^1$H nmr δ10.1 (broad, 3, HO and NH), 7.3 (m, 5, aryl), 5.8 (d, 1, J = 24Hz, CH), 2.9 (s, 3, CH$_3$), 2.6 (s, 3, CH$_3$).

EXAMPLE 7

1,4-Dimethyl-3-(4-hydroxy-3-methoxyphenyl)-2-phenoxy-1,4,2-diazaphospholidin-5-one-2-oxide

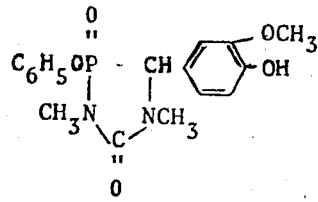

A mixture of 76.1g (0.5 mole) of vanillin, 44.0g (0.5 mole) of 1,3-dimethylurea, and 155.0g (0.5 mole) of triphenyl phosphite in 200g of benzene is stirred under N$_2$ and warmed at reflux (95°) for 1 hr. About half of the benzene is distilled to give a yellow solution: $^{31}$P nmr −25.3 ppm. The reaction mixture solidifies while standing for several days. Additional benzene is added to aid in breaking up the solid. Filtration gives 64.0g of slightly yellow solid. Recrystallization of an 11.0g portion from acetonitrile gives 5.2g of white solid: mp 168°–170°; $^{31}$P nmr −24.5 ppm; molecular weight 362 (mass spectrum) (theory 362).

Anal. Calcd for C$_{17}$H$_{19}$N$_2$O$_5$P: C, 56.35; H, 5.29; N, 7.73; P, 8.55. Found: C, 56.03; H, 5.10; N, 7.66; P, 8.34.

EXAMPLE 8

α-(1,3-Dimethylureido)benzylphosphonic acid.

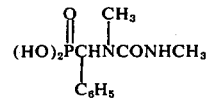

A mixture of 155.2g (0.5 mole) of freshly distilled triphenyl phosphite, 53.0g (0.5 mole) of benzaldehyde, and 44.1g (0.5 mole) of 1,3-dimethylurea in 150g of toluene is stirred under N$_2$ and warmed. Heat of reaction is noticeable at ~80°, and cooling is used for ~10 minutes to keep the temperature below 85°. The reaction mixture is warmed at reflux (117°) for 1.25 hr and then stripped to 140°/0.15mm to give crude 1,4-dimethyl-3-phenyl-2-phenoxy-1,4,2-diazaphospholidim-5-one-oxide which solidifies when cooled, $^{31}$P nmr −24.4, −21.9, and −20.0 ppm (~8:1:1 areas). Acetonitrile (150ml) and 36.0g (2.0 moles) of distilled water are added, and the solution is warmed at reflux for several hours. Solid that forms during warming is separated by filtration of the hot reaction mixture, giving 104.5g (80.9% yield), mp 178°–181° (with foaming). Recrystallization of a portion from isopropyl alcohol gives a white solid: mp 181°–182° (with foaming); $^{31}$P nmr (DMSO-d$_6$) −18.1 ppm (d, J$_{P-H}$ = 24Hz); $^1$H nmr δ9.6 (broad singlet, 3, OH and NH), 7.3 (m, 5, C$_6$H$_5$), 5.7 (d, 1, J$_{H-P}$ = 24Hz), 2.9 (s, 3, NCH$_3$), 2.6 (s, 3, NCH$_3$); acidity, 2.01 equiv/mole, pK$_1$ = 2.20, pK$_2$ = 8.62.

Anal. Calcd for C$_{10}$H$_{15}$N$_2$O$_4$P: C, 46.51; H 5.85; N, 10.85; P, 11.99. Found: C, 46.60; H, 5.78; N, 10.79; P, 12.10. Phenol, 109.9g (78% yield), is isolated from the distillate and filtrate.

EXAMPLE 9

1-(1,3-Dimethylureido)-2-ethylhexylphosphonic acid

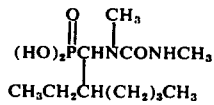

A mixture of 88.1g (1.0 mole) of 1,3-dimethylurea, 269.5g (1.0 mole) of tris(2-chloroethyl) phosphite, and 135g (1.05 moles) of 2-ethylhexaldehyde is warmed at 105°–110° for 2 hr, giving a clear colorless solution: $^{31}$P nmr −30.8 and −28.2 ppm (~2:1 areas). Four-fifths of the reaction mixture is dissolved in 200ml of cyclohexane containing 34.5g of $H_2O$, and the mixture is warmed at 82° for 0.5 hr. Filtration after cooling, and extraction of the solid with hot acetonitrile gives 54.7g of white solid (100.8g more separates from the filtrate while standing): mp 184°–186° dec; $^{31}$P nmr ($CD_3SOCD_3$) −23.5 ppm(m); $^1$H nmr δ9.8 (broad, 2, O$\underline{H}$), 4.4 (d of d, 1, J = 10 and 20Hz, PCH), 2.7 (s, 3, NCH$_3$), 2.5 (s, 3, NCH$_3$), 0.5–2.0 (broad, 15, hexyl); acidity 1.985 equiv/mole, $pK_1 = 1.76$, $pK_2 = 5.29$.

Anal. Calcd for $C_{11}H_{25}N_2O_4P$: C, 47.13; H, 8.99; N, 9.99; P, 11.05. Found: C, 47.41; H, 9.59; N 10.03; P, 11.34.

EXAMPLE 10

α-(1,3-Dimethylureido)-4-hydroxy-3-methoxybenzylphosphonic acid

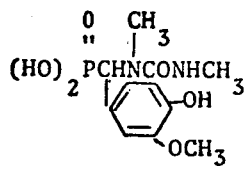

A solution of 10.0g of 1,4-dimethyl-3-(4-hydroxy-3-methoxyphenyl)-2-phenoxy-1,4,2-diazaphospholidin-5-one-2-oxide in 90g of acetonitrile and 10g of water was warmed at reflux for 0.5 hr, and then most of the solvent was allowed to evaporate. The residue was recrystallized twice from ethanol to give 4.6g of white solid: mp 183°–184° (dec); $^{31}$P nmr ($CD_3SOCD_3$) −18.6 ppm (d, J = 24Hz); $^1$H nmr δ10.0 (broad, 3, OH), 5.7 (d, 1, J = 24Hz, CH), 3.8 (s, 3, OCH$_3$), 2.9 (s, 3, NCH$_3$), 2.7 (s, 3, NCH$_3$); 6.7–7.3 (m, 4, aryl and HN).

EXAMPLE 11

1-(1,3-Dimethylureido)-3-(methylthio)propylphosphonic acid

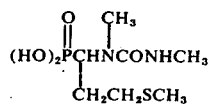

When a mixture of 0.5 mole each of 1,3-dimethylurea, triphenyl phosphite, and 3-methylthiopropionaldehyde in 100g of toluene is warmed to 75°, a reaction is initiated and the temperature increases rapidly to 120°. After further warming at 105° for 1 hr, the resulting yellow solution has a $^{31}$P nmr signal only at −28.2 ppm. After the solvent and most of the by-product phenol are removed by stripping to 110°/1mm, one-third of the residue is dissolved in 75ml of acetonitrile and 10g of water, and this solution is refluxed for 3 hr. The reaction mixture is allowed to evaporate to dryness, and the residue is extracted with ether and then with hot acetonitrile and recrystallized twice from acetic acid to give a white solid: mp 164.5°–167°; $^{31}$P nmr (DMSO-$d_6$) −21.4 ppm; $^1$H nmr δ9.6 (broad, 2, OH), 4.5 (m, 1, PCH), 2.8 (s, NCH$_3$), 2.6 (s, NCH$_3$), 2.0 (s, SCH$_3$), 1.9–2.6 (m, C$\underline{H}_2$C$\underline{H}_2$S).

EXAMPLE 12

1-(1,3-Dimethylureido)-3,7-dimethylocta-2,6-dienyl-1-phosphonic acid

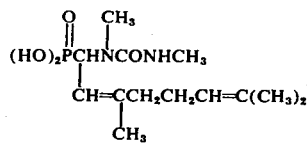

A mixture of 44.0g (0.5 mole) of 1,3-dimethylurea, 135g (0.5 mole) of tris(2-chloroethyl) phosphite, and 76.1g (0.5 mole) of citral is warmed at 95°–105° for 3.75 hr. Water, 54g (3.0 moles), is added, and warming is continued at 75°–90° for 1 hr more. The reaction mixture is diluted with 200ml of acetonitrile and allowed to stand at room temperature for 12 hr. Solid that forms is extracted twice with hot acetonitrile, giving 17.6g, 155°–157° dec. Recrystallization from acetic acid gives a white solid: mp 157°–159° dec; $^{31}$P ($CD_3SOCD_3$) −20.8 ppm (m); acidity 1.97 equiv/mole, $pK_1 = 3.85$, $pK_2 = 9.29$.

Anal. Calcd for $C_{13}H_{25}N_2O_4P$: C, 51.29; H, 8.28; N, 9.20; P, 10.18. Found: C, 51.03; H, 8.75; N, 9.05; P, 10.15.

EXAMPLE 13

[α-(1,3-Dimethylureido)-2,4-dichlorobenzyl]phenylphosphinic acid

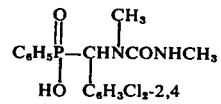

A suspension of 14.4g (0.039m) of 3-(2,4-dichlorophenyl)-1,4-dimethyl-2-phenyl-1,4,2-diazaphospholidin-5-one-2-oxide in 120ml of ethanol is stirred as 0.04m of NaOH (1.0 molar solution) is added dropwise. The solid starting material goes into solution and then another solid separates after a few minutes. This is separated by suction filtration, washed with ethanol, and then extracted with hot acetonitrile to give the sodium salt, a white solid, mp ~294° dec.; $^{31}$P nmr ($D_2O$) −25.8 ppm; $^1$H nmr δ7.05 –8.15 (m, 8, aryl), 5.8 (d, 1, J = 14Hz, PCH), 3.0 (s, 3, NCH$_3$), 2.6 (s, 3, NCH$_3$). A solution of 8.5g of this salt in 200ml of $H_2O$ is stirred as 5g of trifluoroacetic acid is added dropwise. Solid separates immediately. It is recrystallized from acetonitrile to give a white solid, mp 178°; $^{31}$P nmr (DMSO-$d_6$) −31.7 ppm; $^1$H nmr δ7-8.5 (m, 8, aryl), 6.1

(d, 1, J = 14Hz, PCH), 2.9 (s, 3, NCH₃), 2.5 (s, 3, NCH₃); acidity 0.98 equiv/mole, pK$_a$ 4.12.

Anal. Calcd for $C_{16}H_{17}Cl_2N_2O_3P$: C, 49.63; Cl, 18.31; N, 7.23; P, 8.00 Found: C, 49.72; H, 4.49; Cl, 18.58; N, 7.29; P, 8.12.

EXAMPLE 14

1,4-Dimethyl-3-(2-furanyl)-2-phenoxy-1,4,2-diazaphospholidin-5-one-2-oxide

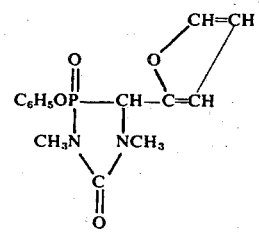

Under conditions similar to those used for the preparation of Example 7 except that furfural is used as the aldehyde reactant, the subject compound is obtained as a white solid: mp 129°–131°; ³¹P nmr (CDCl₃) −20.9 ppm; ¹H δ6.4–7.4 (m, 8, aryl), 4.8 (d, 1, J = 20Hz, CH), 3.0 (d, 3, J = 8Hz, CH₃NP), 2.8 (s, 3, CH₃NCH); ms m/e 306(29) molecular ion, 213(6), 156(100), 108(24).

EXAMPLE 15

When a portion of the product of Example 14 is dissolved in acetonitrile and the solution is treated with water and warmed, (1,3-dimethylureido) (2-furanyl)-methylphosphonic acid is produced.

EXAMPLE 16

1,4-Dimethyl-2-phenyl-1,4,2-diazaphospholidin-5-thione-2-oxide

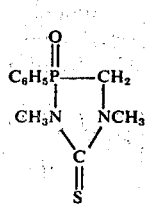

A mixture of 31.2g (0.3 mole) of 1,3-dimethylthiourea, 88.3g (0.3 mole) of diphenyl phenylphosphonite and 13.5g of paraformaldehyde in 80g of toluene is stirred under N₂ and warmed at reflux for 3 hr. After standing overnight, the reaction mixture is filtered to remove a small amount of solid, and the filtrate is stripped to 120°/0.2mm. The residue is extracted twice with ether and once with cyclohexane, and the remaining insoluble material is recrystallized twice from acetonitrile to give 32g (44% yield) of white solid: mp 170°–172°; ³¹P nmr −31.5 ppm; ¹H nmr δ7.6 (m, 5, C₆H₅), 3.88 (d, 1, J = 11.6Hz, HCH), 3.85 (d, 1, J = 8.2Hz, HCH), 3.4 (d, 3, J = 1.2Hz, CH₂NCH₃), 3.0 (d, 3, J = 7.2Hz, PNCH₃); ms 240 (molecular ion).

Anal. Calcd for $C_{10}H_{13}N_2OPS$: C, 49.98; H, 5.45; N, 11.66; P, 12.89; S, 13.34. Found: C, 50.00; H, 5.33; N, 11.67; P, 12.92; S, 13.20.

EXAMPLE 17

(1,3-Dimethylthioureidomethyl)phenylphosphinic acid

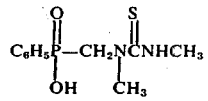

A mixture of 1,4-dimethyl-2-phenyl-1,4,2-diazaphospholidin-5-thione-2-oxide and 40ml of ethanol is stirred as 0.035m of NaOH (10 molar solution) is added dropwise. Solid dissolves during the NaOH addition. The reaction mixture is allowed to evaporate to dryness, and the residue is washed with ether to give crude sodium salt, a white solid: mp 242°–260°; ³¹P nmr (D₂O) −24.7 ppm; ¹H nmr δ7.2 (m, 5, C₆H₅), 3.9 (d, 2, J = 8Hz, CH₂), 3.0 (s, 3, CH₃), 2.9 (s, 3, CH₃). A 5.0 g portion is dissolved in 80 ml of distilled water, and the solution is stirred as 2.2g of trifluoroacetic acid is added dropwise. A white solid that separates after a few minutes is recrystallized from acetonitrile: mp 161°–163°; ³¹P nmr (DMSO-d₆) −31.2 ppm; ¹H nmr δ7.3 −8.4 (m, 6, C₆H₅ and OH), 4.3 (d, 2, J = 7Hz, CH₂), 3.1 (s, 3, CH₃), 2.9 (s, 3, CH₃); acidity 0.990 equiv/mole, pKa = 4.05.

EXAMPLE 18

1,4-Dimethyl-2-phenoxy-1,4,2-diazaphospholidin-5-one-2-oxide

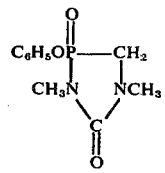

A mixture of 22.0g (0.25 mole) of 1,3-dimethylurea, 8.6g of paraformaldehyde, and 77.5g (0.25 mole) of triphenyl phosphite in 100g of benzene is warmed to 80° where heat of reaction is evident, and cooling is needed for a few minutes to keep the temperature below 84°. The reaction mixture is warmed at reflux for 1 hr and then stripped to 105°/0.5mm to remove solvent and part of the by-product phenol. Solid that separates upon cooling is isolated by filtration and then recrystallized three times from diglyme to give 23.2g of white solid: mp 124°–128°; ³¹P nmr −23.4 ppm; ¹H nmr δ7.2 (m, 5, aryl), 3.6 (d, 2, J = 15Hz, CH₂), 2.9 (d, 3, J = 8Hz, CH₃NP), 2.9 (d, 3, J = 1Hz, CH₃NCH₂) (decoupling from phosphorus converts all three doublets to singlets); mass spectrum (70 eV) m/e (rel intensity) 240(63) (molecular ion), 211(2), 183(1), 147(12), 140(99), 90(100), 56(5), 47(23), 42(86).

Anal. Calcd for $C_{10}H_{13}N_2O_3P$: C, 50.00; H, 5.46; N, 11.66; P, 12.89. Found: C, 49.98; H, 5.63; N, 11.63; P, 12.70.

EXAMPLE 19

(1,3-Dimethylureido)methylphosphonic acid

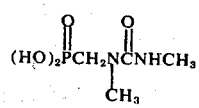

A solution of 12.0g (0.05 mole) of the product of Example 18 in 90g of acetonitrile and 10g of water is refluxed for 1 hr. Solid that separates upon cooling is stirred in boiling acetonitrile, and the mixture is filtered while hot to give 7.4g (82%) of white solid: mp 168°–169° (dec.); $^{31}$P nmr (CD$_3$SOCD$_3$) −20.0 ppm; $^1$H nmr δ9.5 (broad ~3, HO and HN), 3.5 (d, 2, J = 10Hz, CH$_2$), 2.9 (s, 3, CH$_3$), 2.6 (s, 3, CH$_3$).

Anal. Calcd for C$_4$H$_{11}$N$_2$O$_4$P: C, 26.38; H, 6.09; N, 15.38; P, 17.01. Found: C, 26.54; H, 6.16; N, 15.27; P, 17.17.

This phosphonic acid is prepared in a similar manner using tris(2-chloroethyl) phosphite as the phosphorus ester reactant. The crude intermediate 1,4-dimethyl-2-(2-chloroethoxy)-1,4,2-diazaphospholidin-5-one-2-oxide ($^{31}$P nmr −24.9 ppm) is hydrolyzed without isolation from the reaction mixture to give the acid: mp 171°–172° dec. (acetic acid-water).

EXAMPLE 20

1,4-Dimethyl-3-(4-bromo-2-fluorphenyl)-2-(2-naphthyl)-1,4,2-diazaphospholidin-5-one-2-oxide

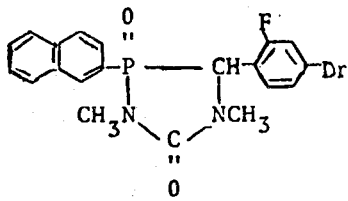

When an equimolar mixture of diphenyl 2-naphthylphosphonite, 4-bromo-2-fluorobenzaldehyde and 1,3-dimethylurea in toluene is warmed at reflux for 1 hour, followed by cooling in an ice bath, a white solid product forms. A portion of this solid is dissolved in ethanol and an equivalent amount of sodium hydroxide (10 molar solution) is added dropwise to the stirred solution. The reaction mixture is allowed to evaporate to dryness, and the residue is washed with ether, giving a crude sodium phosphinate salt. This salt is stirred in distilled water as slightly more than one equivalent of trifluoroacetic acid is added. The product is separated by filtration and then washed with water and recrystallized, giving [α-(1,3-dimethylureido)-4-bromo-2-fluorobenzyl]-2-naphthylphosphinic acid.

The amides of the present invention are useful as biological toxicants. The following example illustrates the use of the amide of Example 3 as a typical product.

Pre-emergent herbicidal activity of representative compounds of this invention is determined by the following procedure:

A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 10 lbs. per acre. The pans are then placed on a sand bench in the greenhouse and watered from below as needed. The plants are observed at the end of approximately 14 days and the results recorded.

Pre-emergent activity of the compound prepared in the designated Example is observed against the species as shown in the table below, wherein X denotes that herbicidal activity is observed.

| PRE-EMERGENT TESTING OF AMIDE OF EXAMPLE 3 | |
|---|---|
| Canada Thistle | X |
| Downy Brome | X |

EXAMPLE 21

The phosphorus amides of the present invention are useful as lead scavengers in leaded gasolines. For this purpose the esters are used in quantities of from 0.05 to 10 moles per mole of lead in the gasoline.

Another area of utility of the phosphorus amides of this invention is for fire-retardancey of paper. The test procedure is as follows: strips (6 by 2 inches) of paper (Whatman filter paper No. 3) are dried in an oven at 130°C. for 10 minutes and then weighed. The weighed strips of paper are placed in glass bottles containing about 50cc. of a solution of ethyl alcohol having 10 to 20% of the phosphorus amide. The bottles are tilted if necessary to cover the paper strips completely with impregnating solution. After one minute the paper is removed and pressed between two paper tissues with a 100 gram weight. The paper strips are dried in air for two minutes and then in an oven at 130°C. for 10 minutes and weighed. The paper treated in this way usually contains from 5 to 15% of the additive amide chemical. Standard burning tests show that the samples having above about 10% of the additive phosphorus amides are significantly more resistant to burning than untreated control samples.

Fire retardant properties are obtained with:

3-(2,4-Dichlorophenyl)-1,4-dimethyl-2-phenyl-1,4,2-diazaphospholidin-5-one-2-oxide.

1,4-Dimethyl-2,3-diphenyl-1,4,2-diazaphospholidin-5-one-2-oxide.

3-(4-Cyanophenyl)-1,4-dimethyl-2-phenyl-1,4,2-diazaphospholidin-5-one-2-oxide.

3-(2,4-dichlorophenyl)-1,4-dimethyl-2-phenyl-1,4,2-diazaphospholidin-5-one-2-oxide.

1,4-Dimethyl-2-phenyl-1,4,2-diazaphospholidin-5-thione-2oxide.

1,4-Dimethyl-3-(4-bromo-2-fluorophenyl)-2-(2-naphthyl)-1,4,2-diazaphospholidin-5-one-2-oxide.

What is claimed is:

1. Cyclic organophosphorus amides having the structure:

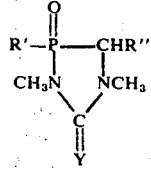

where R' is phenyl or naphthyl, R" is hydrogen, phenyl, and substituted phenyl forms where the substituent is fluorine, chlorine, bromine or mixtures of such substituents, and Y is O or S.

2. 3-(2,4-Dichlorophenyl)-1,4-dimethyl-2-phenyl-1,4,2-diazaphospholidin-5-one-2-oxide.

3. 1,4-Dimethyl-2,3-diphenyl-1,4,2,-diazaphospholidin-5-one-2-oxide.

4. 3-(2,4-dichlorophenyl)-1,4-dimethyl-2-phenyl-1,4,2-diazaphospholidin-5-one-2-oxide.

5. 1,4-Dimethyl-2-phenyl-1,4,2-diazaphospholidin-5-thione-2-oxide.

6. 1,4-Dimethyl-3-(4-bromo-2-fluorophenyl)-2-(2-naphthyl)-1,4,2-diazaphospholidin-5-one-2-oxide.

* * * * *